United States Patent [19]
Barth et al.

[11] Patent Number: 6,028,084
[45] Date of Patent: Feb. 22, 2000

[54] PYRAZOLE DERIVATIVES, METHOD FOR PREPARING SAME, AND PHARMACEUTICAL COMPOSITIONS CONTAINING SAID DERIVATIVES

[75] Inventors: Francis Barth, Montpellier; Christian Congy, Saint Gely Du Fesc; Serge Martinez, Montpellier; Murielle Rinaldi, Saint Georges D'Orques, all of France

[73] Assignee: Sanofi-Synthelabo, Paris, France

[21] Appl. No.: 09/068,869

[22] PCT Filed: Nov. 21, 1996

[86] PCT No.: PCT/FR96/01847

§ 371 Date: May 19, 1998

§ 102(e) Date: May 19, 1998

[87] PCT Pub. No.: WO97/19063

PCT Pub. Date: May 29, 1997

[30] Foreign Application Priority Data

Nov. 23, 1995 [FR] France ................................. 95 13956

[51] Int. Cl.[7] ....................... A61K 31/445; C07D 401/12
[52] U.S. Cl. ......................... 514/326; 514/278; 514/341; 514/406; 546/16; 546/211; 548/374.1
[58] Field of Search ...................... 514/278, 326, 514/341, 406; 546/16, 211; 548/374.1

[56] References Cited

U.S. PATENT DOCUMENTS

| | | | |
|---|---|---|---|
| 3,449,350 | 6/1969 | Walker | 548/374.1 |
| 5,420,141 | 5/1995 | Boigegrain et al. | 514/314 |
| 5,462,960 | 10/1995 | Barth et al. | 514/406 |
| 5,502,059 | 3/1996 | Labeeuw et al. | 514/296 |
| 5,523,455 | 6/1996 | Labeeuw et al. | 558/418 |
| 5,585,497 | 12/1996 | Labeeuw et al. | 548/374.1 |

FOREIGN PATENT DOCUMENTS

| | | |
|---|---|---|
| 664281 | 6/1993 | Australia . |
| 78999/94 | 11/1994 | Australia . |
| 0 477 049 | 3/1992 | European Pat. Off. . |
| 0 576 357 | 12/1993 | European Pat. Off. . |
| 0 647 629 | 4/1995 | European Pat. Off. . |
| 0 656 354 | 6/1995 | European Pat. Off. . |
| 0 658 546 | 6/1995 | European Pat. Off. . |

OTHER PUBLICATIONS

Ward et al. Preparation of 3-aroyl-2-(2-morpholinoethylO . . . )CA 115:208004, 1991.

Varga et al. "Mechanism of the hypotensive action of the hypotensive action of anandamide . . . " CA 125:292640, 1996.

Lan et al. "Structure–activity relationship of pyrazole . . . " J. Med. Chem. 42, pp. 769–776, 1999.

*Primary Examiner*—Ceila Chang
*Attorney, Agent, or Firm*—Michael D. Alexander

[57] ABSTRACT

Compounds of formula (I), wherein $R_1$ is fluorine, hydroxy, $(C_{1-5})$ alkoxy, $(C_{1-5})$ alkylthio, hydroxy$(C_{1-5})$alkoxy, a $-NR_{10}R_{11}$, group, cyano, $(C_{1-5})$ alkyl-sulphonyl or $(C_{1-5})$ alkylsulphinyl; $R_2$ and $R_3$ are each $(C_{,4})$ alkyl or, taken together with the nitrogen atom to which they are attached, form a saturated or unsaturated 5- to 10-membered heterocyclic radical optionally substituted one or more times by $(C_{1-3})$ alkyl or $(C_{1-3})$ alkoxy; each of $R_4$, $R_5$, $R_6$, $R_7$, $R_8$ and $R_9$ is independently hydrogen, halogen or trifluoromethyl, and when $R_1$ is fluorine, $R_4$, $R_5$, $R_6$, $R_7$, $R_8$ and/or $R_9$ may also be fluoromethyl; with the proviso that at least one of substituents $R_4$ or $R_7$. is other than hydrogen; each of $R_{10}$ and $R_{11}$ is independently hydrogen or $(C_{1-5})$ alkyl, or $R_{10}$ and $R_{11}$, taken together with the nitrogen atom to which they are attached, form a heterocyclic radical selected from pyrrolidin-1-yl, piperidin-1-yl, morpholin-4-yl or piperazin-1-yl optionally substituted by $(C_{1-4})$ alkyl; a method for preparing same, and pharmaceutical compositions containing said compounds, are disclosed. Said compounds have very high affinity for central cannabinoid receptors.

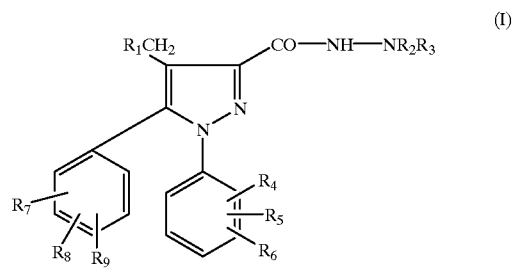

(I)

11 Claims, No Drawings

PYRAZOLE DERIVATIVES, METHOD FOR PREPARING SAME, AND PHARMACEUTICAL COMPOSITIONS CONTAINING SAID DERIVATIVES

The present invention relates to novel pyrazole derivatives and their salts, to a method of preparing them and to pharmaceutical compositions containing them.

Numerous pyrazole derivatives have been described in the literature; more particularly, EP-A-268 554 and DE-A-3 910 248 claim pyrazoles possessing herbicidal properties, EP-A-430 186 and JP-A-3 031 840 claim compounds useful for photography, and EP-A-418 845 claims pyrazoles possessing anti-inflammatory, analgesic and antithrombotic activity.

Patent applications EP-A-576 357 and EP-A-658 546 describe pyrazole derivatives which have an affinity for the cannabinoid receptors. More particularly, patent application EP-A-656 354 claims N-piperidino-5-(4-chlorophenyl)-1-(2,4-dichlorophenyl)-4-methylpyrazole-3-carboxamide, or SR 141 716, and its pharmaceutically acceptable salts, which have a very good affinity for the central cannabinoid receptors.

Novel pyrazole-3-carboxamide derivatives have now been found which possess a very good affinity for the central cannabinoid receptors and are useful in the therapeutic areas in which cannabis is known to be involved.

These compounds can also be used as pharmacological tools, in animals or humans, for detecting and labeling the central cannabinoid receptors.

$\Delta^9$-THC is the main active constituent extracted from *Cannabis sativa* (Tuner, 1985; in Marijuana, 84, Ed. Harvey, DY, IRL Press, Oxford).

The effects of cannabinoids are due to an interaction with high affinity specific receptors present in the central nervous system (Devane et al., Molecular Pharmacology, 1988, 34, 605–613) and in the peripheral nervous system (Nye et al., The Journal of Pharmacology and Experimental Therapeutics, 1985, 234, 784–791; Kaminski et al., 1992, Molecular Pharmacology, 42, 736–742; Munro et al., Nature, 1993, 365, 61–65).

Characterization of the receptors of the central nervous system has been made possible by the development of synthetic ligands for the cannabinoid receptors, such as the agonists WIN 55212-2 (J. Pharmacol. Exp. Ther., 1993, 264, 1352–1363) or CP 55,940 (J. Pharmacol. Exp. Ther., 1988, 247, 1046–1051).

According to one of its aspects, the present invention relates to the compounds of the formula

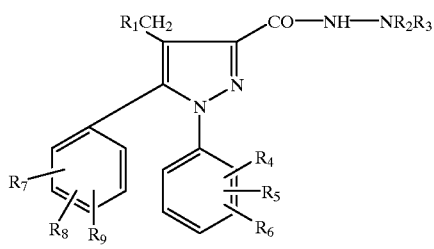

(I)

in which:

R$_1$ is a fluorine, a hydroxyl, a (C$_1$–C$_5$)alkoxy, a (C$_1$–C$_5$) alkylthio, a hydroxy(C$_1$–C$_5$)alkoxy, a group —NR$_{10}$R$_{11}$, a cyano, a (C$_1$–C$_5$)alkylsulfonyl or a (C$_1$–C$_5$)alkylsulfinyl;

R$_2$ and R$_3$ are a (C$_1$–C$_4$)alkyl or, together with the nitrogen atom to which they are bonded, form a 5- to 10-membered, saturated or unsaturated heterocyclic radical which is unsubstituted or monosubstituted or polysubstituted by a (C$_1$–C$_3$)alkyl or by a (C$_1$–C$_3$) alkoxy;

R$_4$, R$_5$, R$_6$, R$_7$, R$_8$ and R$_9$ are each independently hydrogen, a halogen or a trifluoromethyl, and if R$_1$ is a fluorine, R$_4$, R$_5$, R$_6$, R$_7$, R$_8$ and/or R$_9$ can also be a fluoromethyl, with the proviso that at least one of the substituents R$_4$ or R$_7$ is other than hydrogen; and R$_{10}$ and R$_{11}$ are each independently hydrogen or a (C$_1$–C$_5$) alkyl, or R$_{10}$ and R$_{11}$, together with the nitrogen atom to which they are bonded, form a heterocyclic radical selected from pyrrolidin-1-yl, piperidin-1-yl, morpholin-4-yl and piperazin-1-yl, which is unsubstituted or substituted by a (C$_1$–C$_4$)alkyl;

and their salts and their solvates.

(C$_1$–C$_3$)alkyl, (C$_1$–C$_5$)alkyl, (C$_1$–C$_5$)alkoxy and (C$_1$–C$_5$) alkylthio are understood as meaning linear or branched C$_1$–C$_3$ or C$_1$–C$_5$ alkyl radicals or, respectively, alkoxy or alkylthio radicals.

Halogen is understood as meaning chlorine, fluorine, bromine or iodine, preferably chlorine.

5- or 10-membered, saturated or unsaturated heterocyclic radical is understood as meaning a fused or bridged, mono-, di- or tri-cyclic, non-aromatic heterocyclic radical. These radicals include the following in particular: pyrrolidin-1-yl, piperidin-1-yl, hexahydroazepin-1-yl, 2-azabicyclo[2.2.2]oct-5-en-2-yl, 2-azaadamant-2-yl, 1,2,3,6-tetrahydropyridin-1 azabicyclo[2.2.1]heptan-2-yl and 2-azabicyclo[2.2.2]octan-2-yl.

The salts of the compound of formula (I) include the pharmaceutically acceptable acid addition salts such as the hydrochloride, hydrobromide, sulfate, hydrogensulfate, dihydrogenphosphate, methanesulfonate, methylsulfate, maleate, oxalate, fumarate, naphthalene-2-sulfonate, glyconate, gluconate, citrate, isethionate and paratoluenesulfonate.

Advantageously the present invention relates to the compounds of the formula

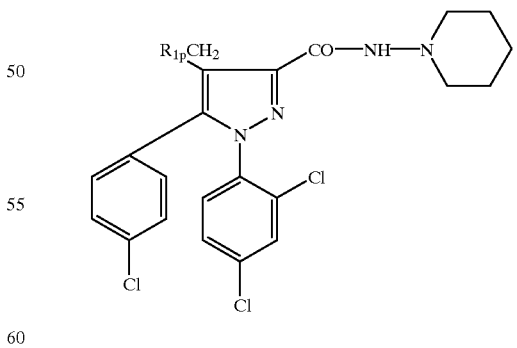

(Ip)

in which R$_{1p}$ is a fluorine, a methoxy or a methylthio, and their salts and their solvates.

According to another of its aspects, the present invention relates to a method of preparing the compounds of formula (I) above, their salts and their solvates; this method, called method 1, is characterized in that:

a) a brominated ester of the formula

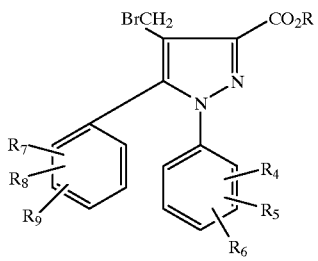

(II)

in which $R_4$, $R_5$, $R_6$, $R_7$, $R_8$ and $R_9$ are as defined above and R is a ($C_1$–$C_4$)alkyl, is treated with a compound of the formula $R'_1A$ (III), in which $R'_1$, is $R_1$ as defined for (I), or a precursor of $R_1$, and A is a hydrogen or a cation;

b1) in the resulting ester, $R'_1$ is optionally converted to $R_1$;

b2) the ester obtained in step a) or step b 1), of the formula

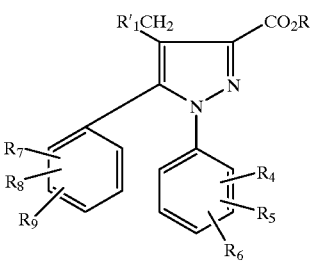

(IV)

is saponified;

c) the resulting acid of the formula

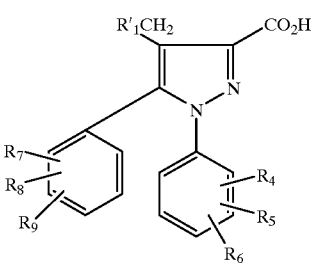

(V)

or a functional derivative of this acid, is treated with a hydrazine of the formula $H_2N$—$NR_2R_3$ (VI), in which $R_2$ and $R_3$ are as defined for (I);

d1) in the resulting compound, $R'_1$ is optionally converted to $R_1$; and d2) the compound obtained in step c) or step d1), of the formula

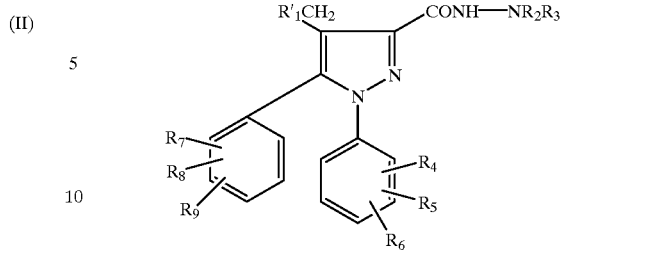

(I')

is optionally converted to one of its salts or one of their solvates.

Precursor of $R_1$ is understood as meaning a group which can be converted to $R_1$ in a subsequent step. This conversion can be effected on the ester of formula (IV) obtained in step a) or on the compound of formula (I') obtained in step c).

Thus, in one variant of the method, called method 2, a compound of formula (I) in which $R_1=R_{1a}$ and is a group selected from a fluorine, a ($C_1$–$C_5$)alkoxy, a ($C_1$–$C_5$) alkylthio, a hydroxy($C_1$–$C_5$)alkoxy, a cyano and a group $NR_{10}R_{11}$, in which $R_{10}$ and $R_{11}$ are as defined above, can be prepared from a compound of formula (I') in which $R'_1$=OH.

The brominated esters of formula (II) are described in European patent application EP-A-658 546. They are prepared by reacting N-bromosuccinimide with a compound of the formula

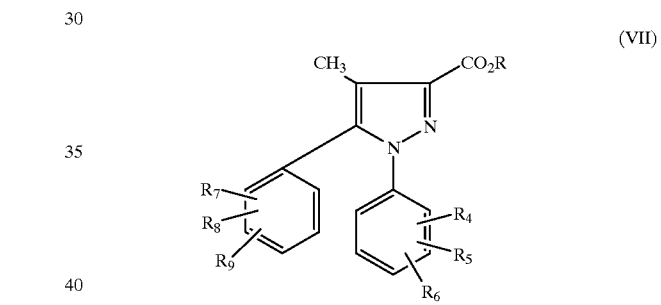

(VII)

in a solvent such as carbon tetrachloride, in the presence of benzoyl peroxide.

The preparation of the compounds of formula (VII) is also described in patent application EP-A-658 546.

The hydrazines $H_2N$—$NR_2R_3$ are known or are prepared by known methods.

For example, they can be obtained by the method described in Chem. Ber., 1986, 119, 1413–1423, which consists in reducing a nitroso derivative of the formula ON—$NR_2R_3$ (VIII), in which $R_2$ and $R_3$ are as defined above for (I), with a hydride such as lithium aluminum hydride. The nitroso derivative (VIII) is obtained by reacting a compound of the formula $HNR_2R_3$ (IX), in which $R_2$ and $R_3$ are as defined above for (I), with sodium nitrite in aqueous solution, in the presence of an acid such as acetic acid.

1-Aminopiperidine is commercially available.

2-Amino-2-azabicyclo[2.2.2]oct-5-ene is prepared according to Chem. Ber., 1986, 119, 1413–1423.

2-Amino-2-azaadamantane is prepared from 2-azaadamantane via the nitroso derivative.

2-Azaadamantane is prepared according to J. Org. Chem., 1981, 46, 4953.

In the definition of A, cation is understood as meaning an alkali metal or alkaline earth metal cation or a quaternary ammonium group such as tetraethylammonium.

As the functional derivative of the acid (V), it is possible to use the acid chloride, the anhydride, a mixed anhydride, a $C_1$–$C_4$ alkyl ester, in which the alkyl is linear or branched, an activated ester, for example the p-nitrophenyl ester, or the free acid appropriately activated, for example with N,N-dicyclohexylcarbodiimide, benzotriazol-N-oxotris (dimethylamino)phosphonium hexafluorophosphate (BOP) or silicon tetrachloride (Synth. Commun., 1986, 16, 1261).

Thus, in step c) of the method according to the invention, the pyrazole-3-carboxylic acid chloride, obtained by reacting thionyl chloride with the acid of formula (V), can be reacted with a hydrazine $H_2N$—$NR_2R_3$ (VI) in a solvent such as dichloromethane, under an inert atmosphere, at a temperature between 0° C. and room temperature, in the presence of a base such as triethylamine.

One variant of the procedure of step c) consists in preparing the mixed anhydride of the acid of formula (V) by reacting ethyl chloroformate with the acid of formula (V), in the presence of a base such as triethylamine, and in reacting the mixed anhydride with hydrazine in a solvent such as dichloromethane, under an inert atmosphere, at room temperature, in the presence of a base such as triethylamine.

To prepare a compound of formula (I) in which $R_1$=OH, the reactant $R'_1A$ (III) used is an alkali metal or alkaline earth metal hydroxide such as sodium hydroxide or potassium hydroxide, in which case the acid of formula (V) is obtained directly.

Thus method 2 according to the invention is characterized in that:

e) a brominated ester of the formula

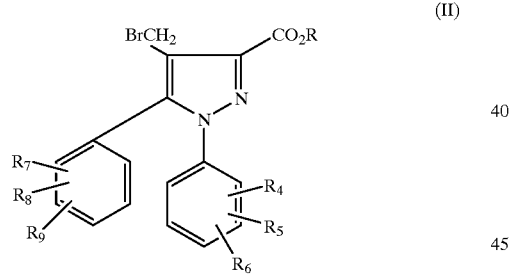

(II)

in which $R_4$, $R_5$, $R_6$, $R_7$, $R_8$, $R_9$ and R are as defined above, is treated with an alkali metal or alkaline earth metal hydroxide;

f) the resulting acid of the formula

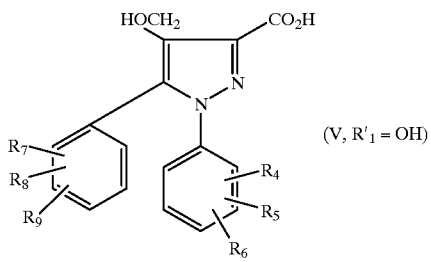

(V, $R'_1$ = OH)

or a functional derivative of this acid, is treated with a hydrazine of the formula $H_2N$—$NR_2R_3$ (VI), in which $R_2$ and $R_3$ are as defined for (I);

g) the resulting compound of the formula

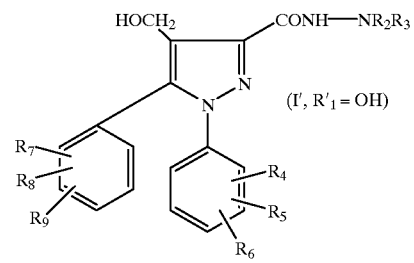

(I', $R'_1$ = OH)

is treated with a compound of the formula Hal—B, in which Hal is a halogen, preferably chlorine, and B is a mesyl, tosyl or trifluoromethanesulfonyl radical;

h) the resulting compound of the formula

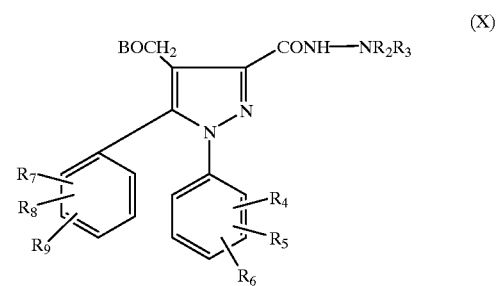

(X)

is treated with a compound of the formula $R_{1a}A$ (XI), in which $R_{1a}$ is as defined above and A is a hydrogen or a cation; and i) the resulting compound of the formula

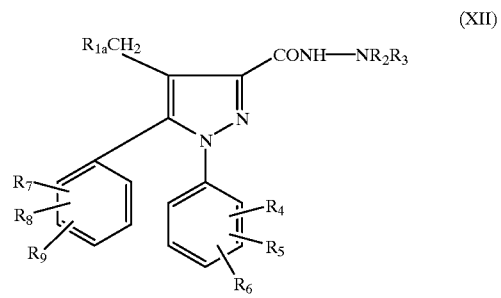

(XII)

is optionally converted to one of its salts or one of their solvates.

To prepare a compound of formula (I) in which $R_1$ is a ($C_1$–$C_5$)alkoxy, the reactant of formula (III) or (XI) used is a $C_1$–$C_5$ alcohol in the presence of a non-nucleophilic base such as a metal hydride like sodium or potassium hydride. Depending on the meanings of $R_1$ and R, a mixture of esters is obtained in step a) of method 1 and is saponified in step b2) to give the acid of formula (V).

To prepare a compound of formula (I) in which $R_1$ is a ($C_1$–$C_5$)alkylthio, the reactant of formula (III) or (XI) used is a $C_1$–$C_5$ thioalcohol in the presence of a non-nucleophilic base such as a metal hydride like sodium or potassium hydride.

If appropriate, the ester of formula (IV) obtained in step a) or the compound of formula (XII) obtained in step h) in which $R'_1$ or, respectively, $R_{1a}$ is a ($C_1$–$C_5$)alkylthio can be converted, by reaction with an oxidizing agent such as hydrogen peroxide or metachloroperbenzoic acid, to give a compound of formula (IV) or, respectively, formula (I) in which $R_1$ is a $(C_1-C_5)$alkylsulfonyl or a $(C_1-C_5)$alkylsulfinyl.

To prepare a compound of formula (I) in which $R_1$ is a cyano, the reactant of formula (III) or (XI) used can be a metal cyanide such as sodium cyanide, or a quaternary ammonium cyanide, for example tetraethylammonium cyanide; in the latter case, the nucleophilic substitution reaction of step a) or step h) is carried out in the presence of a phase transfer catalyst.

To prepare a compound of formula (I) in which $R_1$ is fluorine, the reactant of formula (III) or (XI) used can be a fluorinating agent; fluorinating agents which may be mentioned are a quaternary ammonium fluoride such as tetrabutylammonium fluoride; a metal fluoride, for example potassium fluoride, used in the presence of a weak base like potassium carbonate and a complexing agent like Kryptofix®; or a hydrofluoric acid complex, for example an $(HF)_n$-tertiary amine complex, where n=1, 2 or 3, such as $(HF)_3$—$N(C_2H_5)_3$. A compound of formula (I) in which $R_1$=F is preferably prepared by fluorinating a compound of formula (I) in which $R_1$=OH: it is possible either to carry out a direct fluorination, for example with diethylamino sulfide trifluoride, or, according to method 2, to prepare a compound of formula (X) as an intermediate and then fluorinate this with an agent such as one of the fluorinating agents described above.

More particularly, a compound of formula (I) in which $R_1$=F is preferably prepared by method 1 from an ester of formula (II) using potassium fluoride (R'$_1$A=KF) as the compound of formula (III), in the presence of a complexing agent like Kryptofix®.

In particular, a compound of formula (I) in which $R_1$ is a fluorine and $R_4$, $R_5$, $R_6$, $R_7$, $R_8$ and/or $R_9$ are a fluoromethyl is prepared using, as the starting material, a compound of formula (II) in which $R_4$, $R_5$, $R_6$, $R_7$, $R_8$ and/or $R_9$ are a bromomethyl. Fluorination, effected by one of the methods described above, makes it possible to convert $R_4$, $R_5$, $R_6$, $R_7$, $R_8$ and/or $R_9$ to fluoromethyl. The starting compound of formula (II) is prepared by reacting N-bromosuccinimide with a compound of formula (VII) in which $R_4$, $R_5$, $R_6$, $R_7$, $R_8$ and/or $R_9$ are a methyl.

To prepare a compound of formula (I) in which $R_1$ is a group —$NR_{10}R_{11}$, an amine of the formula $HNR_{10}R_{11}$ (III) can be reacted in step a). A compound of formula (I) in which $R_1$=$NR_{10}R_{11}$ is preferably prepared by method 2 from a compound of formula (I') in which R'$_1$=OH by intermediate conversion of the alcohol to mesyloxy, tosyloxy or trifluoromethanesulfonyloxy, followed by reaction with an amine $HNR_{10}R_{11}$, in the presence of a non-nucleophilic base such as a metal hydride like sodium hydride.

The compound of formula (I) obtained by the method according to the invention is isolated, in the form of the free base or a salt or solvate, by the conventional techniques.

The compound of formula (I) can be isolated in the form of one of its salts, for example the hydrochloride or the oxalate; in this case the free base can be prepared by neutralizing said salt with a mineral or organic base such as sodium or ammonium hydroxide, triethylamine or an alkali metal carbonate or bicarbonate like sodium or potassium carbonate or bicarbonate, and converted to another salt such as the methanesulfonate, the fumarate or the naphthalene-2-sulfonate.

If the compound (I) is obtained in the form of the free base, salification is effected by treatment with the chosen acid in an organic solvent. Treatment of the free base, dissolved for example in an ether such as diethyl ether or in acetone, with a solution of the acid in the same solvent gives the corresponding salt, which is isolated by the conventional techniques.

The compounds of formula (I) possess a very good in vitro affinity for the central cannabinoid receptors under the experimental conditions described by Devane et al., Molecular Pharmacology, 1988, 34, 605–613.

More particularly, the compounds of the present invention, as such or in the form of one of their pharmaceutically acceptable salts, are potent and selective central cannabinoid receptor antagonists with a Ki of between 1 and 100 nM. They are between 100 and 1000 times more active on the central receptors than on the peripheral receptors, are active via oral administration and pass through the blood-brain barrier.

The good penetration of the compounds of the present invention into the central nervous system has been demonstrated by ex vivo binding experiments with [$^3$H]-CP 55940 under the conditions described by M. Rinaldi-Carmona et al., Life Sciences, 1995, 56, 1941–1947.

Furthermore, their antagonistic nature has been demonstrated by the results obtained with the adenylyl cyclase inhibition model and the mouse vas deferens contraction model, as described by M. Rinaldi-Carmona et al., FEBS Letters, 1994, 350, 240–244.

By virtue of their remarkable properties, especially their high affinity, their selectivity for the central receptor and their capacity to penetrate the blood-brain barrier, the compounds (I), as such or optionally in the form of pharmaceutically acceptable salts or in the form of solvates, can be used as the active principles of drugs for combating diseases of the central nervous system in mammals.

The toxicity of the compounds (I) is compatible with their use as psychotropic drugs, especially for the treatment of thymic disorders, anxiety disorders, humoral disorders, vomiting, memory disorders, cognitive disorders, neuropathies, migraine, stress, diseases of psychosomatic origin, epilepsy, dyskinesia or Parkinson's disease.

The compounds (I) according to the invention can also be used as drugs for the treatment of appetite disorders, especially as anorexigenics, and for the treatment of schizophrenia, delirium disorders, psychotic disorders in general and disorders associated with the use of psychotic substances. Furthermore, the compounds (I) according to the invention can be used as drugs for anticancer chemotherapy.

The compounds (I) according to the invention, as such or in radiolabeled form, can also be used as pharmacological tools, in humans or animals, for detecting and labeling the central cannabinoid receptors. In particular, the compounds of formula (I) in which $R_1$ is a radioactive fluorine atom, such as $^{18}$F, can be used in positron emission tomography studies in order to visualize in vivo the location and density of the central cannabinoid receptors and study the pharmacokinetics and biodistribution of central cannabinoid receptor agonists or antagonists.

Furthermore, the compounds of formula (I) containing an OH group, such as those comprising a group $R_1$=OH or $R_1$=hydroxy($C_1$–$C_5$)alkoxy, can be used as intermediates for the preparation of irreversible ligands comprising photoactivatable groups or electrophilic groups, for example an azido, an isothiocyanato, a halogenoacetamido, a Michael acceptor or an aldol ester. These irreversible ligands can be used to isolate, purify and characterize the cannabinoid receptors and identify their active site.

The compounds of formula (I) containing an OH group, such as those comprising a group $R_1$=OH or $R_1$=hydroxy ($C_1$–$C_5$)alkoxy, can also be used as intermediates for the preparation of central cannabinoid receptor ligands containing a group detectable by immunochemical methods, for example the biotinyl group. These ligands can be used to detect, characterize and purify the central cannabinoid receptors.

The compounds according to the invention are generally administered in dosage units.

Said dosage units are preferably formulated into pharmaceutical compositions in which the active principle is mixed with a pharmaceutical excipient.

Thus, according to another of its aspects, the present invention relates to pharmaceutical compositions containing, as the active principle, a compound of formula (I), one of its pharmaceutically acceptable salts or one of their solvates.

The compounds of formula (I) above and their pharmaceutically acceptable salts can be used in daily doses of 0.01 to 100 mg per kilogram of body weight of the mammal to be treated, preferably in daily doses of 0.1 to 50 mg/kg. In humans the dose can preferably vary from 0.5 to 4000 mg per day, more particularly from 2.5 to 1000 mg, depending on the age of the subject to be treated or the type of treatment: prophylactic or curative.

In the pharmaceutical compositions of the present invention for oral, sublingual, subcutaneous, intramuscular, intravenous, topical, transdermal, local or rectal administration, the active principle can be administered to animals and humans in unit forms of administration, mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, topical forms of administration, subcutaneous, intramuscular, intravenous, intranasal or intraocular forms of administration and rectal forms of administration.

In the pharmaceutical compositions of the present invention, the active principle is generally formulated in dosage units containing from 0.5 to 1000 mg, advantageously from 1 to 500 mg and preferably from 2 to 200 mg of said active principle per dosage unit for daily administrations.

When a solid composition is prepared in the form of tablets, a wetting agent such as sodium laurylsulfate can be added to the micronized or non-micronized active principle and the whole is mixed with a pharmaceutical vehicle such as silica, starch, lactose, magnesium stearate, talcum or the like. The tablets can be coated with sucrose, a variety of polymers or other appropriate substances, or else they can be treated so as to have a sustained or delayed activity and so as to release a predetermined amount of active principle continuously.

A preparation in the form of gelatin capsules is obtained by mixing the active principle with a diluent, such as a glycol or a glycerol ester, and incorporating the resulting mixture into soft or hard gelatin capsules.

A preparation in the form of a syrup or elixir can contain the active principle together with a sweetener, which is preferably calorie-free, methylparaben and propylparaben as antiseptics, a flavoring and an appropriate color.

The water-dispersible powders or granules can contain the active principle mixed with dispersants or wetting agents or with suspending agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral administration is effected using aqueous suspensions, isotonic saline solutions or injectable sterile solutions containing pharmacologically compatible dispersants and/or solubilizing agents, for example propylene glycol or polyethylene glycol.

Thus, to prepare an aqueous solution for intravenous injection, it is possible to use a cosolvent—an alcohol such as ethanol or a glycol such as polyethylene glycol or propylene glycol—and a hydrophilic surfactant such as Tween® 80. To prepare an oily solution for intramuscular injection, the active principle can be solubilized with a triglyceride or a glycerol ester.

Local administration can be effected using gels, ointments or creams.

Transdermal administration can be effected using patches in multilaminar form or reservoirs in which the active principle is in alcoholic solution.

The active principle can also be formulated as microcapsules or microspheres, optionally with one or more carriers or additives.

The active principle can also be presented in the form of a complex with a cyclodextrin, for example α-, β- or γ-cyclodextrin, 2-hydroxypropyl-β-cyclodextrin or methyl-β-cyclodextrin.

Among the sustained release forms useful in the case of chronic treatments, it is possible to use implants. These can be prepared in the form of an oily suspension or in the form of a suspension of microspheres in an isotonic medium.

The Examples which follow illustrate the invention without however implying a limitation.

The melting or decomposition points of the products, m.p., are measured in a capillary tube with a Tottoli apparatus.

The NMR spectra are run at 200 MHz in DMSO.

The following abbreviations are used in the Preparations and in the Examples:
THF: tetrahydrofuran
$CCl_4$: carbon tetrachloride
Ether: diethyl ether
$(iPr)_2O$: iso ether: diisopropyl ether
EtOH: ethanol
AcOEt: ethyl acetate
MeOH: methanol
DCM: dichloromethane
NaOH: sodium hydroxide
$NaHCO_3$: sodium hydrogencarbonate
$NH_4Cl$: ammonium chloride
NaH: sodium hydride
$MgSO_4$: magnesium sulfate
KOH: potassium hydroxide
Kryptofix®: 4,7,13,16,21 ,24-hexaoxa-1,10-diazabicyclo [8.8.8]hexacosane
AcOH: acetic acid
HCl: hydrochloric acid
$H_2SO_4$: sulfuric acid
NaCl: sodium chloride
BOP: benzotriazol-N-oxotris(dimethylamino)phosphonium hexafluorophosphate
RT: room temperature
M.p.: melting point
TFA: trifluoroacetic acid The following abbreviations are used in the interpretation of the NMR spectra:
s: singlet
bs: broad singlet
d: doublet
dd: doublet of doublets t: triplet
q: quadruplet
m: multiplet or unresolved signals

PREPARATION 1

Methyl 5-(4-chlorophenyl)-1-(2,4-dichlorophenyl)-4-bromomethylpyrazole-3-carboxylate A) Methyl 5-(4-chlorophenyl)-1-(2,4-dichlorophenyl)-4-methylpyrazole-3-carboxylate 19.54 g of 5-(4-chlorophenyl)-1-(2,4-dichlorophenyl)-4-methylpyrazole-3-carboxylic acid are dissolved in 350 ml of MeOH, 0.97 g of paratoluenesulfonic acid is added and the mixture is then refluxed for 18 hours. After evaporation of the solvent, the residue is taken up with AcOEt and washed with saturated NaHCO₃ solution and then with saturated NaCl solution. It is dried over MgSO₄, the insoluble material is filtered off and the filtrate is then concentrated to dryness to give 18.53 g of the expected compound, m.p.=133° C.

B) Methyl 5-(4-chlorophenyl)-1-(2,4-dichlorophenyl)-4-bromomethylpyrazole-3-carboxylate 4.05 g of N-bromosuccinimide and 20 mg of benzoyl peroxide are added to a solution of 9 g of the compound of the previous step in 110 ml of CCl₄ and the mixture is refluxed for 19 hours. The solution is filtered and the filtrate is then washed with water and with saturated NaCl solution and then dried over MgSO₄. After evaporation of the solvent, the foam obtained is taken up with (iPr)₂O at RT and dried under vacuum. The white solid obtained is recrystallized from (iPr)₂O to give 5.96 g of the expected compound, m.p.=145° C.

PREPARATION 2

5-(4-Chlorophenyl)-1-(2,4-dichlorophenyl)-4-hydroxymethylpyrazole-3-carboxylic acid 2 g of the compound of PREPARATION 1 are placed in 30 ml of THF, 30 ml of 5% NaOH are added and the mixture is then refluxed for 17 hours. After cooling, the reaction medium is poured into 200 ml of 5% HCl at 0° C., extracted with DCM, washed with saturated NaCl solution and then dried over MgSO₄ to give 1.79 g of the expected product (amorphous solid).

PREPARATION 3

5-(4-Chlorophenyl)-1-(2,4-dichlorophenyl)-4-((2-hydroxyethoxy)methyl)-pyrazole-3-carboxylic acid A) 2-Hydroxyethyl 5-(4-chlorophenyl)-1-(2,4-dichlorophenyl)-4-((2-hydroxy-ethoxy)methyl)pyrazole-3-carboxylate 2 g of the compound of PREPARATION 1 are placed in 80 ml of THF, and 1.2 ml of ethylene glycol and 201 mg of NaH are added in 2 portions at 0° C. under nitrogen. The mixture is allowed to warm up to RT and then refluxed for 20 hours. After evaporation of the solvent, the residue is taken up with saturated NH₄Cl solution, extracted with AcOEt, washed with water and dried over MgSO₄. The residue is chromatographed on silica using MeOH/DCM (1/99 to 2/98; v/v) as the eluent to give 640 mg of the expected product.

B) 5-(4-Chlorophenyl)-1-(2,4-dichlorophenyl)-4-((2-hydroxyethoxy)methyl)-pyrazole-3-carboxylic acid 670 mg of the compound obtained in the previous step are placed in 20 ml of MeOH, 0.19 g of potassium hydroxide in 18 ml of water is then added and the mixture is refluxed for 5 hours. After the reaction medium has returned to RT, 100 ml of 5% HCl are added. The precipitate formed is filtered off, washed with water and dried under vacuum to give 420 mg of the expected compound, m.p.=182° C.

PREPARATION 4

5-(4-Chlorophenyl)-1-(2,4-dichlorophenyl)-4-(methylthiomethyl)pyrazole-3-carboxylic acid A) Methyl 5-(4-chlorophenyl)-1-(2,4-dichlorophenyl)-4-(methylthiomethyl)-pyrazole-3-carboxylate 1.09 g of the compound of PREPARATION 1 are placed in 15 ml of THF, and 0.19 g of sodium methylthiolate is added. After stirring for 6 days at RT, the mixture is diluted with 50 ml of water and then extracted with AcOEt and washed with saturated NaCl solution to give 0.90 g of the expected compound (amorphous solid).

B) 5-(4-Chlorophenyl)-1-(2,4-dichlorophenyl)-4-(methylthiomethyl)pyrazole-3-carboxylic acid The compound of the previous step (0.90 g) is placed in 15 ml of MeOH, 0.29 g of potassium hydroxide in 10 ml of water is added and the mixture is refluxed for 3 hours. The reaction medium is poured into 100 ml of iced water and acidified to pH 2 by the addition of 5% HCl. The white solid obtained is filtered off, washed with water and dried under vacuum to give 0.78 g of the expected product (amorphous solid).

PREPARATION 4 bis 5-(4-Chlorophenyl)-1-(2,4-dichlorophenyl)-4-(methylthiomethyl)pyrazole-3-carboxylic acid chloride 0.78 g of the acid of PREPARATION 4 is placed in 15 ml of toluene, 0.49 ml of thionyl chloride is added and the mixture is then refluxed for 3 hours. The solvent is evaporated off under vacuum, the residue is taken up with 30 ml of toluene and the solvent is evaporated off again under vacuum (twice) to give 1 g of the expected product.

PREPARATION 5

5-(4-Chlorophenyl)-1-(2,4-dichlorophenyl)-4-methoxymethylpyrazole-3-carboxylic acid A solution containing 1 g of the compound of PREPARATION 1 in 30 ml of MeOH and 0.14 g of sodium methylate is prepared and refluxed for 18 hours. 0.24 g of potassium hydroxide in 5 ml of water is added and the mixture is refluxed for a further 2 hours. It is concentrated under vacuum, diluted with 20 ml of water and acidified to pH 2 by the addition of 10% HCl. The white solid formed is filtered off and washed with water to give 0.82 g of the expected product, m.p.=95° C.

PREPARATION 5 bis 5-(4-Chlorophenyl)-1-(2,4-dichlorophenyl)-4-methoxymethylpyrazole-3-carboxylic acid chloride The acid of PREPARATION 5 (0.82 g) is placed in 30 ml of toluene, 0.54 ml of thionyl chloride is added and the mixture is then refluxed for 2 hours. It is evaporated to dryness, the residue is taken up with 20 ml of toluene and the solvent is evaporated off to dryness again (twice). The white foam obtained is used directly in a subsequent step to prepare a compound according to the invention.

PREPARATION 6 tert-Butyl 5-(4-chlorophenyl)-1-(2,4-dichlorophenyl)-4-bromomethyl-pyrazole-3-carboxylate A) tert-Butyl 5-(4-chlorophenyl)-1-(2,4-dichlorophenyl)-4-methylpyrazole-3-carboxylate A solution of 5 g of 5-(4-chlorophenyl)-1-(2,4-dichlorophenyl)-4-methylpyrazole-3-carboxylic acid in 35 ml of dioxane is introduced into a 250 ml autoclave and then cooled to −10° C. 2 ml of concentrated $H_2SO_4$ and 70 ml of 2-methylpropene, cooled to −10° C., are then added and the autoclave is closed, allowed to warm up to RT and then heated at 40° C. for 18 hours, with vigorous stirring. After cooling to RT, the reaction mixture is concentrated under vacuum, the residue is extracted with DCM, the organic phase is washed with water, with 5% $Na_2CO_3$ solution and with saturated NaCl solution and dried over $MgSO_4$ and the solvent is evaporated off under vacuum. The residue is chromatographed on silica using a toluene/AcOEt mixture (from 90/10 to 80/20; v/v) as the eluent to give 3.15 g of the expected product, m.p.=112° C.

B) tert-Butyl 5-(4-chlorophenyl)-1-(2,4-dichlorophenyl)-4-bromomethylpyrazole-3-carboxylate 1.94 g of N-bromosuccinimide and 10 mg of benzoyl peroxide are added to a solution of 4.28 g of the compound obtained in the previous step in 86 ml of $CCl_4$ and the mixture is then refluxed for 16 hours. After cooling to RT, the insoluble material is filtered off and the filtrate is concentrated under vacuum to give 2.48 g of the expected product, m.p.=139° C.

PREPARATION 7

5-(4-Chlorophenyl)-1-(2,4-dichlorophenyl)-4-cyanomethylpyrazole-3-carboxylic acid A) tert-Butyl 5-(4-chlorophenyl)-1-(2,4-dichlorophenyl)-4-cyanomethylpyrazole-3-carboxylate 0.229 g of tetraethylammonium cyanide is added to a solution of 0.6 g of the compound obtained in PREPARATION 6 in 20 ml of DCM and the reaction mixture is refluxed for 5 hours. It is washed with water, with saturated $Na_2CO_3$ solution and with saturated NaCl solution, the organic phase is dried over $MgSO_4$ and the solvent is evaporated off under vacuum. The residue is chromatographed on silica using an AcOEt/toluene mixture (5/95; v/v) as the eluent to give 0.55 g of the expected product, m.p.=168° C.

B) 5-(4-Chlorophenyl)-1-(2,4-dichlorophenyl)-4-cyanomethylpyrazole-3-carboxylic acid A mixture of 0.55 g of the compound obtained in the previous step and 3 ml of TFA is stirred for 30 minutes at RT. It is concentrated under vacuum, the residue is extracted with DCM, the organic phase is washed with saturated NaCl solution and dried over $MgSO_4$ and the solvent is evaporated off under vacuum to give 0.341 g of the expected product.

PREPARATION 7 bis 5-(4-Chlorophenyl)-1-(2,4-dichlorophenyl)-4-cyanomethylpyrazole-3-carboxylic acid chloride 0.91 ml of thionyl chloride is added dropwise to a mixture of 0.91 g of the compound obtained in PREPARATION 7 and 20 ml of toluene and the resulting mixture is then refluxed for 1 hour. It is concentrated under vacuum, the residue is taken up with toluene and the solvent is evaporated off under vacuum to give 1.1 g of the expected product.

PREPARATION 8

Ethyl 5-(4-chlorophenyl)-1-(2,4-dichlorophenyl)-4-bromomethylpyrazole-3-carboxylate 4.8 g of N-bromosuccinimide and 20 mg of benzoyl peroxide are added to a solution of 10.73 g of ethyl 5-(4-chlorophenyl)-1-(2,4-dichlorophenyl)-4-methylpyrazole-3-carboxylate in 200 ml of $CCl_4$ and the mixture is then refluxed for 16 hours. The insoluble material is filtered off and the filtrate is concentrated under vacuum. The residue is extracted with DCM, the organic phase is washed with water and dried over $MgSO_4$ and the solvent is evaporated off under vacuum to give 14.13 g of the expected product.

PREPARATION 9

5-(4-Chlorophenyl)-1-(2,4-dichlorophenyl)-4-(methylsulfonylmethyl)-pyrazole-3-carboxylic acid A) Ethyl 5-(4-chlorophenyl)-1-(2,4-dichlorophenyl)-4-(methylthiomethyl)-pyrazole-3-carboxylate A solution of 3 g of the compound obtained in PREPARATION 8 and 0.68 g of sodium methylthiolate in 40 ml of THF is refluxed for 5 days. It is hydrolyzed by the addition of 50 ml of water, the THF is concentrated under vacuum, the residual aqueous phase is extracted with DCM, the organic phase is washed with saturated NaCl solution and dried over $MgSO_4$ and the solvent is evaporated off under vacuum to give 2.51 g of the expected product.

B) Ethyl 5-(4-chlorophenyl)-1-(2,4-dichlorophenyl)-4-(methylsulfonylmethyl)-pyrazole-3-carboxylate A solution of 1.96 g of m-chloroperbenzoic acid at a concentration of 50% in 25 ml of DCM is added dropwise to a solution of 2.51 g of the compound obtained in the previous step in 25 ml of DCM and the reaction mixture is then refluxed for 16 hours. It is extracted with DCM, the organic phase is washed with water, with 5% $Na_2CO_3$ solution and with saturated NaCl solution and dried over $Na_2SO_4$ and the solvent is evaporated off under vacuum. The residue is chromatographed on silica using a toluene/AcOEt mixture (80/20; v/v) as the eluent to give 0.68 g of the expected product.

C) 5-(4-Chlorophenyl)-1-(2,4-dichlorophenyl)-4-(methylsulfonylmethyl)pyrazole-3-carboxylic acid A solution of 0.25 g of KOH in 20 ml of water is added to a solution of 0.65 g of the compound obtained in the previous step in 20 ml of MeOH and the reaction mixture is then refluxed for 1 hour. It is poured into 50 ml of 10% HCl solution cooled to 0° C., and the precipitate formed is filtered off, washed with water and dried under vacuum to give 0.68 g of the expected product.

PREPARATION 9 bis 5-(4-Chlorophenyl)-1-(2,4-dichlorophenyl)-4-(methylsulfonylmethyl)-pyrazole-3-carboxylic acid chloride 0.5 g of thionyl chloride is added to a solution of 0.53 g of the compound obtained in PREPARATION 9 in 3 ml of toluene and the mixture is then refluxed for 1 hour. It is concentrated under vacuum, the residue is taken up with 5 ml of toluene and the solvent is evaporated off under vacuum to give 0.53 g of the expected product.

PREPARATION 10

5-(4-Chlorophenyl)-1-(2,4-dichlorophenyl)-4-fluoromethylpyrazole-3-carboxylic acid A) Methyl 5-(4-chlorophenyl)-1-(2,4-dichlorophenyl)-4-fluoromethylpyrazole-3-carboxylate 0.51 g of Kryptofix® and 0.79 g of dry potassium fluoride are added successively to a solution of 0.65 g of the compound obtained in PREPARATION 1 in 50 ml of dry acetonitrile and the mixture is then refluxed for 1 hour. It is concentrated under vacuum, the residue is taken up with 30 ml of water and extracted with 30 ml of AcOEt, the organic phase is washed with saturated NaCl solution and dried over $MgSO_4$ and the solvent is evaporated off under vacuum to give 0.57 g of the expected product in the form of a white solid, m.p.=114° C.

B) 5-(4-Chlorophenyl)-1-(2,4-dichlorophenyl)-4-fluoromethylpyrazole-3-carboxylic acid 10 ml of 30% NaOH solution are added at RT to a solution of 0.49 g of the compound obtained in the previous step in 50 ml of MeOH and the reaction mixture is stirred for 10 minutes at RT. It is poured into 60 ml of 2.5% $H_2SO_4$ solution and extracted with DCM, the organic phase is washed with saturated NaCl solution and dried over $MgSO_4$ and the solvent is evaporated off under vacuum to give 0.45 g of the expected product in the form of a white solid, m.p.=60–80° C.

EXAMPLE 1

N-(Piperidin-1-yl)-5-(4-chlorophenyl)-1-(2,4-dichlorophenyl)-4-hydroxy-methylpyrazole-3-carboxamide 1.75 g of the compound of PREPARATION 2 are placed in 30 ml of DCM, and 1.53 ml of triethylamine, 0.50 ml of 1-aminopiperidine and then, at 0° C., 2.33 g of BOP are added successively. The mixture is stirred at 0° C. for 10 minutes and then at RT for 3 and a half hours. The reaction medium is poured into 100 ml of iced water, extracted with DCM, washed with water and with saturated NaCl solution and then dried over $MgSO_4$. The residue obtained is chromatographed on fine silica using AcOEt/toluene (20/80 to 40/60; v/v) as the eluent to give 800 mg of the expected compound, m.p.=118° C.

NMR 1.1 to 1.7 ppm:m:6H 2.7 ppm:t:4H 4.4 ppm:d:2H 5.15 ppm:t:1H 7.1 to 7.45 ppm:AA'-BB' system:4H 7.5 ppm:dd:1H 7.7 ppm:m:2H 9.35 ppm:s:1H

EXAMPLE 2

N-(Piperidin-1-yl)-5-(4-chlorophenyl)-1-(2,4-dichlorophenyl)-4-((2-hydroxyethoxy)methyl) pyrazole-3-carboxamide 0.33 ml of triethylamine, 0.11 ml of 1-aminopiperidine and then, at 0° C., 0.50 g of BOP are added successively to a solution of 420 mg of the compound of PREPARATION 3 in 20 ml of DCM. The mixture is stirred for 10 minutes at 0° C. and then for 3 hours at RT. It is taken up with 120 ml of iced water, extracted with DCM and washed with water and then with saturated NaCl solution. After drying over $MgSO_4$, the residue is chromatographed on fine silica using AcOEt/toluene (20/80 to 40/60; v/v) as the eluent to give 210 mg of the expected compound, m.p.=194° C.

NMR 1.2 to 1.7 ppm:m:6H 2.75 ppm:t:4H 3.45 ppm:m:4H 4.4 to 4.7 ppm:m:3H 7.2 to 7.5 ppm:AA'-BB' system:4H 7.6 ppm:dd:1H 7.7 to 7.8 ppm:m:2H 9.35 ppm:s:1H

EXAMPLE 3

N-(Piperidin-1-yl)-5-(4-chlorophenyl)-1-(2,4-dichlorophenyl)-4-fluoro-methylpyrazole-3-carboxamide A solution of 600 mg of the compound of EXAMPLE 1 in 24 ml of DCM is added dropwise to a solution of 0.19 ml of diethylamino sulfide trifluoride in 24 ml of DCM at −78° C. under nitrogen. The mixture is allowed to warm up slowly to 0° C. and then stirred for one hour at 0° C. The reaction mixture is poured into saturated $NaHCO_3$ solution and then extracted with DCM, washed with saturated NaCl solution and dried over $MgSO_4$. The residue is chromatographed on fine silica using AcOEt/toluene (5/95 to 40/60; v/v) as the eluent to give 250 mg of the expected product, m.p.=184° C.

NMR 1.3 to 1.8 ppm:m:6H 2.85 ppm:t:4H 5.6 ppm:d:2H 7.3 to 7.6 ppm:AA'-BB' system:4H 7.7 ppm:dd:1H 7.85 ppm:d:1H 7.95 ppm:d:1H 9.25 ppm:s:1H This compound can also be prepared by following the procedure described below.

0.036 ml of thionyl chloride is added at RT to a solution of 0.065 g of the compound obtained in PREPARATION 10 in 3 ml of toluene and the reaction mixture is then placed in an oil bath at 70° C. and heated gradually to 120° C. After 5 minutes, nitrogen is bubbled intermittently into the reaction mixture and heating is continued for 10 minutes. The reaction mixture is cooled to RT and concentrated under vacuum. The residue is dissolved in 5 ml of DCM and this solution is added to a solution of 0.021 ml of 1-aminopiperidine and 0.054 ml of triethylamine in 5 ml of DCM, cooled to 0° C. After stirring for 30 minutes at RT, the reaction mixture is poured into 2.5% $H_2SO_4$ solution and extracted with DCM, the organic phase is washed with saturated NaCl solution and dried over $MgSO_4$ and the solvent is evaporated off under vacuum to give 0.07 g of the expected product.

EXAMPLE 4

N-(Piperidin-1-yl)-5-(4-chlorophenyl)-1-(2,4-dichlorophenyl)-4-(methyl-thiomethyl)pyrazole-3-carboxamide 1 g of the compound of PREPARATION 4 bis is placed in 15 ml of DCM and a solution of 0.23 ml of 1-aminopiperidine and 0.29 ml of triethylamine in 15 ml of DCM is added dropwise. After stirring for 16 hours at RT, the mixture is poured into 100 ml of iced water. The resulting mixture is extracted with DCM and washed with water and then with saturated NaCl solution. The product obtained crystallizes from an $(iPr)_2O/DCM$ mixture to give 0.67 g of the expected product, m.p.=183° C.

NMR 1.1 to 1.7 ppm:m:6H 1.8 ppm:s:3H
2.7 ppm:t:4H
3.8 ppm:s:2H
7.1 to 7.4 ppm:AA'-BB' system:4H
7.5 ppm:d:1H
7.65 ppm:s:1H
7.7 ppm:d:1H
9.15 ppm:s:1H

EXAMPLE 5

N-(Piperidin-1-yl)-5-(4-chlorophenyl)-1-(2,4-dichlorophenyl)-4-methoxy-methylpyrazole-3-carboxamide hydrochloride The product obtained in PREPARATION 5 bis is placed in 10 ml of DCM and added dropwise to a solution of 0.24 ml of 1-aminopiperidine and 0.33 ml of triethylamine in 10 ml of DCM, cooled to 0° C. The mixture is stirred for 16 hours at RT and then extracted with DCM and washed with water and then with saturated NaCl solution. The salt is prepared by dissolving the product obtained in ether and adding a saturated solution of hydrochloric acid in ether. The solid obtained is filtered off and then recrystallized from an MeOH/Et$_2$O mixture to give 0.16 g of the expected product, m.p.=198° C.

NMR
1.3 to 1.9 ppm:s:6H
3.25 ppm:t:41H
3.2 ppm:s:3H
4.45 ppm:s:2H
5.9 ppm:bs:1H
7.2 to 7.5 ppm:AA'-BB' system:4H
7.6 ppm:dd:1H
7.7 to 7.9 ppm:m:2H
10.85 ppm:bs:1H

EXAMPLE 6

N-(Piperidin-1-yl)-5-(4-chlorophenyl)-1-(2,4-dichlorophenyl)-4-cyano-methylpyrazole-3-carboxamide A mixture of 1.1 g of the compound obtained in PREPARATION 7 bis, 0.3 ml of 1-aminopiperidine and 0.39 ml of triethylamine in 15 ml of DCM is stirred for 3 hours at RT. The solvent is concentrated under vacuum. The residue is chromatographed on silica using a toluene/AcOEt mixture (95/5; v/v, then 90/10; v/v) as the eluent to give 0.066 g of the expected product after crystallization from iso ether, m.p.123° C.

NMR
1.2 to1.8ppm:m:6H
2.8 ppm:t:4H
4.05 ppm:s:2H
7.2 to 7.5 ppm:AA'-BB' system:4H
7.6 ppm:dd:1H
7.8 ppm:d:1H
7.85 ppm:d:1H
9.45 ppm:s:1H

EXAMPLE 7

N-(Piperidin-1-yl)-5-(4-chlorophenyl)-1-(2,4-dichlorophenyl)-4-(methyl-sulfonylmethyl)pyrazole-3-carboxamide A solution of 0.14 g of 1-aminopiperidine and 1.3 ml of triethylamine in 10 ml of DCM is cooled to 0° C., a solution of 0.53 g of the compound obtained in PREPARATION 9 bis is added dropwise and the reaction mixture is stirred for 3 hours at RT. It is washed with water and with saturated NaCl solution, the organic phase is dried over MgSO$_4$ and the solvent is evaporated off under vacuum. The residue is chromatographed on silica using a toluene/AcOEt mixture (70/30; v/v) as the eluent to give 0.38 g of the expected product, m.p.=171° C.

NMR 1.2 to 1.8 ppm:m:6H
2.85 ppm:t:4H
2.9 ppm:s:3H
4.7 ppm:s:2H
7.4 to 7.6 ppm:AA'-BB' system:4H
7.65 ppm:dd:1H
7.85 ppm:d:1H
7.9 ppm:d:1H
9.45 ppm:s:1H

We claim:

1. Compound of the formula

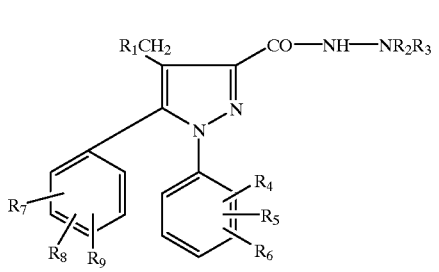

in which:

R$_1$ is a fluorine, a hydroxyl, a (C$_1$–C$_5$)alkoxy, a (C$_1$–C$_5$) alkylthio, a hydroxy(C$_1$–C$_5$)alkoxy, a group —NR$_{10}$R$_{11}$, a cyano, a (C$_1$–C$_5$)alkylsulfonyl or a (C$_1$–C$_5$)alkylsulfinyl;

R$_2$ and R$_3$ are a (C$_1$–C$_4$)alkyl or, together with the nitrogen atom to which they are bonded, form a 5- to 10-membered, saturated or unsaturated heterocyclic radical which is unsubstituted or monosubstituted or polysubstituted by a (C$_1$–C$_3$)alkyl or by a (C$_1$–C$_3$) alkoxy;

R$_4$, R$_5$, R$_6$, R$_7$, R$_8$ and R$_9$ are each independently hydrogen, a halogen or a trifluoromethyl, and if R$_1$ is a fluorine, R$_4$, R$_5$, R$_6$, R$_7$, R$_8$ and/or R$_9$ can also be a fluoromethyl, with the proviso that at least one of the substituents R$_4$ or R$_7$ is other than hydrogen; and R$_{10}$ and R$_{11}$ are each independently hydrogen or a (C$_1$–C$_5$)alkyl, or R$_{10}$ and R$_{11}$ together with the nitrogen atom to which they are bonded, form a heterocyclic radical selected from pyrrolidin-1-yl, piperidin-1-yl, morpholin-4-yl and piperazin-1-yl, which is unsubstituted or substituted by a (C$_1$–C$_4$)alkyl; or its salt or solvate.

2. Compound according to claim 1 of the formula

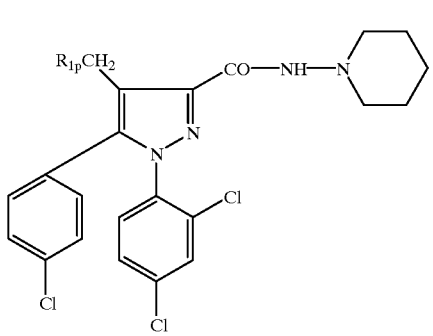

(Ip)

in which $R_{1P}$ is a fluorine, a methoxy or a methylthio, or its salt or solvate.

3. Method of preparing a compound of formula (I) according to claim 1, its salts and their solvates, characterized in that:

a) a brominated ester of the formula

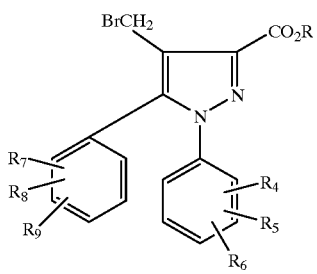

(II)

in which $R_4$, $R_5$, $R_6$, $R_7$, $R_8$ and $R_9$ are as defined for (I) in claim 1 and R is a $(C_1–C_4)$alkyl, is treated with a compound of the formula $R'_1A$ (III), in which $R'_1$ is $R_1$ as defined for (I) in claim 1, or a precursor of $R_1$, and A is a hydrogen or a cation;

b1) in the resulting ester, $R'_1$ is optionally converted to $R_1$;

b2) the ester obtained in step a) or step b1), of the formula

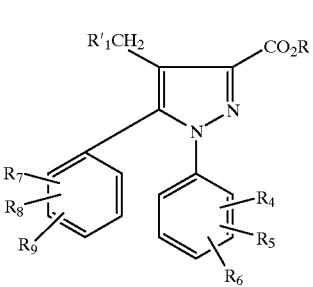

(IV)

is saponified;

c) the resulting acid of the formula

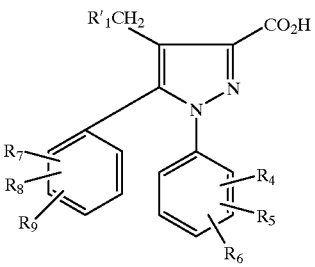

(V)

or a functional derivative of this acid, is treated with a hydrazine of the formula $H_2N$—$NR_2R_3$ (VI), in which $R_2$ and $R_3$ are as defined for (I) in claim 1;

d1) in the resulting compound, $R'_1$ is optionally converted to $R_1$; and d2) the compound obtained in step c) or step d1), of the formula

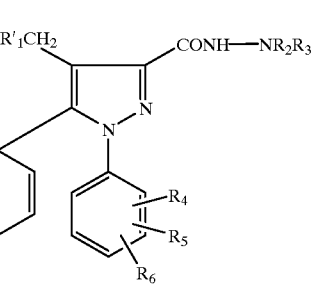

(I')

is optionally converted to one of its salts or one of their solvates.

4. Method of preparing a compound of formula (I) according to claim 1 in which $R_1=R_{1a}$ and is a group selected from a fluorine, a $(C_1–C_5)$alkoxy, a $(C_1–C_5)$alkylthio, a hydroxy $(C_1–C_5)$alkoxy, a cyano and a group —$NR_{10}R_{11}$, in which $R_{10}$ and $R_{11}$ are as defined for (I) in claim 1, characterized in that:

a) a brominated ester of the formula

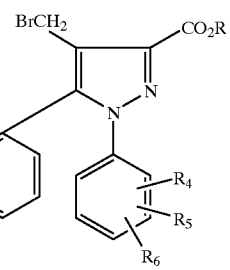

(II)

in which $R_4$, $R_5$, $R_6$, $R_7$, $R_8$, $R_9$ and R are as defined in claim 3, is treated with an alkali metal or alkaline earth metal hydroxide;

b) the resulting acid of the formula

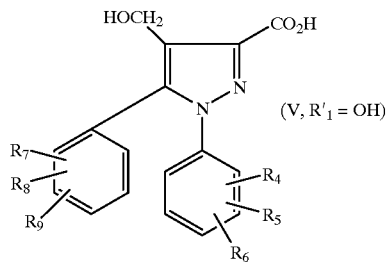

(V, $R'_1$ = OH)

or a functional derivative of this acid, is treated with a hydrazine of the formula $H_2N$—$NR_2R_3$ (VI), in which $R_2$ and $R_3$ are as defined for (I) in claim 1;

c) the resulting compound of the formula

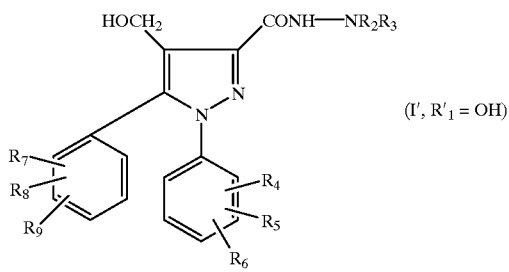

(I', $R'_1$ = OH)

is treated with a compound of the formula Hal—B, in which Hal is a halogen and B is a mesyl, tosyl or trifluoromethanesulfonyl radical;

d) the resulting compound of the formula

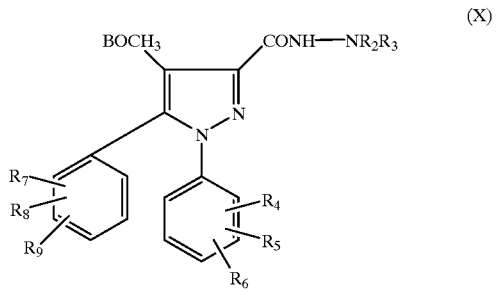

(X)

is treated with a compound of the formula $R_{1a}A$ (XI), in which $R_{1a}$ is as defined above and A is a hydrogen or a cation; and e) the resulting compound of the formula

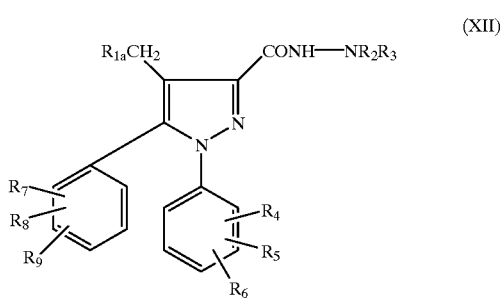

(XII)

is optionally converted to one of its salts or one of their solvates.

5. A pharmaceutical composition comprising a pharmaceutically acceptable carrier and, as the active principle, a therapeutically effective amount of a compound according to one of claim 1 or 2.

6. Pharmaceutical composition according to claim 5 in the form of a dosage unit, in which the active principle is mixed with at least one pharmaceutical excipient.

7. Pharmaceutical composition according to claim 6 containing 0.5 to 1000 mg of active principle.

8. Pharmaceutical composition according to claim 7 containing 2 to 200 mg of active principle.

9. A method for the treatment of diseases in which antagonism of the cannabinoid receptor is involved which comprises administering to a patient in need of such treatment a therapeutically effective amount of a compound according to claim 1 or 2.

10. A method according to claim 9 for the treatment of central nervous system diseases which comprises administering to a patient in need of such treatment an effective amount of a compound according to claim 1 or 2.

11. A method for labeling a cannabinoid receptor comprising exposing said receptor to a compound according to claim 1 or 2 wherein $R_1$ is $^{18}F$.

* * * * *